(12) United States Patent
Copland et al.

(10) Patent No.: US 9,688,959 B2
(45) Date of Patent: Jun. 27, 2017

(54) COMPOSITIONS, USES, AND PREPARATION OF PLATELET LYSATES

(75) Inventors: Ian B. Copland, Decatur, GA (US); Jacques Galipeau, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 14/129,448

(22) PCT Filed: Jun. 26, 2012

(86) PCT No.: PCT/US2012/044211
§ 371 (c)(1),
(2), (4) Date: Dec. 26, 2013

(87) PCT Pub. No.: WO2013/003356
PCT Pub. Date: Jan. 3, 2013

(65) Prior Publication Data
US 2014/0127314 A1    May 8, 2014

Related U.S. Application Data

(60) Provisional application No. 61/501,411, filed on Jun. 27, 2011, provisional application No. 61/547,897, filed on Oct. 17, 2011.

(51) Int. Cl.
| | | |
|---|---|---|
| *A61K 35/14* | (2015.01) | |
| *C12N 5/00* | (2006.01) | |
| *C12N 5/0775* | (2010.01) | |
| *A61K 38/18* | (2006.01) | |
| *A61K 35/19* | (2015.01) | |
| *A61L 15/40* | (2006.01) | |
| *A61L 15/44* | (2006.01) | |
| *A61L 17/00* | (2006.01) | |
| *A61L 24/00* | (2006.01) | |

(52) U.S. Cl.
CPC ........... *C12N 5/0675* (2013.01); *A61K 35/19* (2013.01); *A61K 38/1858* (2013.01); *A61L 15/40* (2013.01); *A61L 15/44* (2013.01); *A61L 17/005* (2013.01); *A61L 24/0005* (2013.01); *A61L 24/0015* (2013.01); *C12N 5/0018* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *A61L 2300/406* (2013.01); *C12N 2502/115* (2013.01)

(58) Field of Classification Search
CPC ............. C12N 5/0675; C12N 5/0018; C12N 2502/115; A61K 35/19; A61K 38/1858; A61L 17/005; A61L 15/44
USPC .......................................... 424/532; 435/408
See application file for complete search history.

(56) References Cited

U.S. PATENT DOCUMENTS

| | | | | |
|---|---|---|---|---|
| 5,198,357 | A * | 3/1993 | Holmovist | C12N 5/163 435/243 |
| 7,951,593 | B2 * | 5/2011 | Gogly | C12N 5/0656 435/325 |
| 8,603,541 | B2 | 12/2013 | Weissman et al. | |
| 8,628,787 | B2 | 1/2014 | Soldani et al. | |
| 2003/0124703 | A1 | 7/2003 | Nur et al. | |
| 2008/0005851 | A1 * | 1/2008 | Perez-Prat Vinuesa | C11D 3/1253 8/115.51 |
| 2009/0023211 | A1 | 1/2009 | Persson et al. | |
| 2009/0305401 | A1 | 12/2009 | Strunk et al. | |
| 2010/0076464 | A1 | 3/2010 | Sheetrit et al. | |
| 2011/0052533 | A1 | 3/2011 | Centeno | |
| 2011/0280952 | A1 | 11/2011 | Caramella et al. | |
| 2012/0156306 | A1 | 6/2012 | Weissman et al. | |
| 2013/0084341 | A1 | 4/2013 | Centeno | |
| 2013/0164737 | A1 | 6/2013 | Rida et al. | |
| 2013/0195959 | A1 | 8/2013 | Patel | |
| 2013/0243878 | A1 | 9/2013 | Mariner et al. | |
| 2013/0287753 | A1 | 10/2013 | Centeno | |
| 2014/0056989 | A1 | 2/2014 | Weissman et al. | |

(Continued)

FOREIGN PATENT DOCUMENTS

| | | |
|---|---|---|
| JP | 2011-508771 A | 3/2011 |
| WO | 2009/087560 A1 | 7/2009 |
| WO | 2010/064267 | 6/2010 |

(Continued)

OTHER PUBLICATIONS

Chao et al. Plateletpheresis by Discontinuous Centrifugation: Effect of Collecting Methods on the In Vitro Function of Platelets; British Journal of Haematology, vol. 39 (1979) pp. 177-187.*

(Continued)

*Primary Examiner* — Scott Long
*Assistant Examiner* — Paul Martin
(74) *Attorney, Agent, or Firm* — Kilpatrick Townsend & Stockton, LLP

(57) ABSTRACT

In certain embodiments, this disclosure describes compositions comprising platelet lysates depleted of fibrinogen. In a further embodiment, the composition further comprises a cell culture medium component. This disclosure also provides a method for preparing the composition, comprising the steps of (a) lysing platelets providing a lysate; (b) removing cell debris; and (c) depleting fibrinogen by forming a removable mass by adding a metal salt such as calcium chloride. Furthermore, the disclosure also describes the product produced using said method.

21 Claims, 5 Drawing Sheets

(56) References Cited

U.S. PATENT DOCUMENTS

2014/0179602 A1 6/2014 Weissman et al.
2014/0335195 A1 11/2014 Houze et al.

FOREIGN PATENT DOCUMENTS

| WO | 2011/148326 | 12/2011 |
| WO | 2012/085910 | 6/2012 |
| WO | 2013/000672 | 1/2013 |
| WO | 2013/073941 | 5/2013 |
| WO | 2014/076200 | 5/2014 |
| WO | 2014/097289 | 6/2014 |

OTHER PUBLICATIONS

Shih et al., "Expansion of adipose tissue mesenchymal stromal progenitors in serum-free medium supplemented with virally inactivated allogeneic human platelet lysate", Transfusion, vol. 51, No. 4, Apr. 1, 2011, pp. 770-778.
Extended European Search Report for European Patent Application No. 12804449.2 mailed Feb. 11, 2015.
Bell et al., Severe Citrate Toxicity Complicating Volunteer Apheresis Platelet Donation, Journal of Clinical Apheresis, 22:15-16 (2007).
Burnouf et al., Blood-derived biomaterials and platelet growth factors in regenerative medicine, Blood Reviews, 27:77-89 (2013).
Copland et al., The effect of platelet lysate fibrinogen on the functionality of MSCs in immunotherapy, Biomaterials, 34:7840-7850 (2013).
Geremicca et al., Blood components for topical use in tissue regeneration: evaluation of corneal lesions treated with platelet lysate and considerations on repair mechanisms, Blood Transfus., 8(2):107-112 (2010).
International Search Report for PCT/US2012/044211, mailed Oct. 18, 2012 (2 pages).
International Preliminary Report on Patentability for PCT/US2012/-44211, mailed Jan. 4, 2014 (5 pages).
PL•Derl et al., Development and validation of a production process of platelet lysate for autologous use, Platelets, 22(3):204-209 (2011).
Quigg et al., Blockade of Antibody-Induced Glomerulonephritis with Crry-Ig, a Soluble Murine Complement Inhibitor, J. Immunol, 160:4553-4560 (1998).
Ranzato et al., Platelet lysate promotes in vitro wound scratch closure of human dermal fibroblasts: different roles of cell calcium, P38, ERK and P13K/AKT, J. Cell. Mol. Med., 13(8B):2030-2038 (2009).
Salvione et al., Influence of heparin on fibrinogen and D-dimer plasma levels in acute myocardial infarction treated with streptokinase, Eur. Heart J., 15(5):654-659 (1994).
Schallmoser et al., Human platelet lysate can replace fetal bovine serum for clinical-scale expansion of functional mesenchymal stromal cells, Transfusion, 47:1436-1446 (2007).
Schallmoser et al., Preparation of Pooled Human Platelet Lysate (pHPL) as an Efficient Supplement for Animal Serum-Free Human Stem Cell Cultures, Journal of Visualized Experiments, 32 pii 1523, URL:http://www.jove.com/details.php?id=1523 (2009).
Schallmoser et al., Generation of a Pool of Human Platelet Lysate and Efficient Use in Cell Culture, Basic Cell Culture Protocols, Methods in Molecular Biology, 946:349-362 (2013).
Somers et al., Stimulation of epithelial healing in chronic postoperative otorrhea using lyophilized cultured keratinocyte lysates, Am. J. Otol., 18(6):702-706 (1997).
Uppal et al., Hyaluronic acid nanofiber wound dressing—production, characterization, and in vivo behavior, J. Biomed. Mater Res. B. Appl. Biomater., 97(1):20-29 (2011).
Yousef et al., Cryoprecipitate production: the use of additives to enhance the yield, Cln. Lab. Haem., 28:237-240 (2006).
Office Action for Japanese Application No. 2014-518918 mailed Mar. 29, 2016 along with an English translation.
Patent Examination Report No. 1 for Australian Patent Application No. 2012275562 mailed Jun. 22, 2016.
Chinese Office Action for Application No. 201280036793.1 mailed Sep. 5, 2016 along with a partial English translation.
Office Action for Japanese Application No. 2014-518918 mailed Nov. 22, 2016 along with an English translation.

* cited by examiner

COMPOSITIONS, USES, AND PREPARATION OF PLATELET LYSATES

CROSS REFERENCE TO RELATED APPLICATIONS

This application is a national stage entry of PCT/US2012/044211, filed on Jun. 26, 2012, now expired, which claims priority to US. Provisional Application No. 61/501,411 filed 27 Jun. 2011 and U.S. Provisional Application No. 61/547,897 filed 17 Oct. 2011, both hereby incorporated by reference in their entirety.

FIELD

In certain embodiments, this disclosure describes compositions comprising platelet lysates depleted of fibrinogen and cryoprecipitate. In a further embodiment, the composition further comprises a cell culture medium component. This disclosure also provides a method for preparing the composition, comprising the steps of (a) lysing platelets providing a lysate; (b) removing cell debris; and (c) depleting fibrinogen by forming a removable mass by adding a metal salt such as calcium chloride. Furthermore, the disclosure also describes the product produced using said method.

BACKGROUND

Regenerative medicine is a broad field in which a multitude of technologies are employed to enhance the body's ability to heal itself. One such technology is cellular therapy. Several cell types have been used for cellular therapy including, but not limited to, embryonic, neonatal, somatic, xenogenic, and induced pluripotent cells. Mesenchymal stem cells (MSCs) in particular have demonstrated therapeutic efficacy by regenerating skeletal tissues such as bone, cartilage, and tendons while also treating neuronal degeneration and supporting hematopoietic engraftment. See, e.g., Doucet et al., J Cell Phys, (2005), 205: 228-236 and Lange et al., J Cell Physiol, (2007), 213: 18-26.

Previous efforts have proliferated donor cells ex vivo using a growth medium containing fetal bovine serum (FBS). The presence of FBS in the culture medium, despite washing the donor cells prior to transfer to the recipient, has led to the generation of antibodies against FBS and has resulted in arthus-like reactions. Selvaggi et al., Blood, (1997), 89(3): 776-9. Concerns regarding the transfer of animal prion, viral, and zoonose contamination also surround the use of FBS. The potential complications associated with using FBS in growth media have generated a particular interest for non-xenogenic growth supplements capable of maintaining the functionality of cells.

Autologous and allogeneic human sera were both tested as a replacement for FBS in efforts to proliferate MSCs ex vivo. Allogeneic serum resulted in cell growth arrest and death of MSCs. Shandadfar et al., Stem Cells, (2005) 23(9): 1357-66. Although autologous serum proliferates MSCs effectively, pragmatic concerns such as cost and availability of serum make this approach somewhat impractical. See, e.g., Kobayashi et al., J Bone Joint Surg Br, (2005), 87(10): 1426-33. Previous investigations indicate that growth factors released from human platelets effectively enhance the growth of several cell types, including MSCs. Consequently, recent efforts have focused upon using platelet lysate in lieu of FBS as a cell culture supplement.

Platelets are capable of releasing multiple growth factors such as multiple platelet-derived growth factors (PDGFs), insulin-like growth factor 1 (IGF-1), and transforming growth factor beta (TGF-$\beta$). Sanchez et al., Int J Oral Maxillofac Implants, (2003), 18(1): 93-103. For purposes of supplementing cell culture media with these growth factors, platelet lysate was shown to be superior to both platelet adhesion and platelet aggregation methodologies. Doucet et al., J Cell Phys, (2005), 205: 228-236.

Despite enhancing cell growth, the use of unprocessed platelet lysate poses its own set of complications. Clinical uses of ex vivo cellular therapy have used FBS as a cell culture growth supplement until recently, and considerations regarding the use of platelet lysate in clinical applications remain to be addressed. These considerations include the presence of cellular debris, clotting factors, and cryoprecipitate as well as the immunosuppressive characteristics of cells cultured in the presence of platelet lysate. Furthermore, the use of unprocessed platelet lysate in cell culture results in the conversion of fibrinogen to fibrin. Generally, heparin is added directly to the cell culture to prevent this conversion. See, e.g., Schallmoser et al., Tissue Eng Part C Methods, (2008), 14(3): 185-96. In spite of this use of heparin, large fibrous strands may form within the media and attach to the MSC monolayer. This carries the risk of infusing patients with these fibrous strands, potentially resulting in micro or macro-occlusions. Thus, there is a need to find improved methods of reducing the generation of fibrous strands.

The zymogen Prothrombin is produced in the liver. It is enzymatically cleaved at two sites by Factor Xa, producing thrombin. Thrombin, in turn, mediates clotting by the conversion of fibrinogen to fibrin. Fibrin may cross-link with the transglutaminase Factor XIII, forming a clot. The fibrin may coalesce into fibrous strands that are hazardous if transferred into a patient, as described above. Heparin may be used to increase the affinity of anti-thrombin for both thrombin and Factor Xa, potentially disrupting the clotting cascade.

SUMMARY

In certain embodiments, this disclosure describes compositions comprising platelet lysates depleted of fibrinogen and cryoprecipitate. In a further embodiment, the composition further comprises a cell culture medium component. This disclosure also provides a method for preparing the composition, comprising the steps of (a) lysing platelets providing a lysate; (b) removing cell debris; and (c) depleting fibrinogen by forming a removable mass by adding a metal salt such as calcium chloride. Furthermore, the disclosure also describes the product produced using said method.

In certain embodiments, the platelet lysate composition is substantially depleted of fibrinogen. In some embodiments, the composition has a concentration of fibrinogen of less than or about 2 or 4 µg/mL. In some embodiments, the composition has a concentration of PDGF-BB of more than about 15, 30, or 40 ng/mL. In some embodiments, the composition does not contain acid citrate dextrose (ACD) or does not contain substantial amounts of a calcium chelating anticoagulant such as acid citrate. In some embodiments, the composition is substantially free of cell debris. In some embodiments, the composition is substantially free of cryoprecipitate. In some embodiments, the composition is substantially depleted of thrombin.

In some embodiments, the disclosure relates to a method of culturing cells using a cell culture media comprising said composition. Typical cell culture media contain amino acids and optionally insulin, hormones, antibiotics, and saccharides. In some embodiments, the cultured cells are somatic, neonatal, embryonic, xenogenic, or pluripotent cells. In some embodiments, the cultured cells are MSCs.

In some embodiments, the disclosure relates to expand cells from species selected from rodent, porcine, primate, human primate, and non-human primate.

In some embodiments, the disclosure relates to a method of preparing the composition, comprising the steps of (a) lysing platelets providing a lysate; (b) removing cell debris; and (c) depleting fibrinogen substantially. In certain embodiments, the method further comprises the step of (d) removal of a calcium chelating anticoagulant, e.g., ACD, and recalcification of the composition. In some embodiments, the cell debris is removed prior to depletion of fibrinogen, after depletion of fibrinogen, or both before and after fibrinogen depletion. In some embodiments, multiple platelet lysates are pooled before removing cell debris, after removing cell debris, when removal of cell debris is incomplete, before depleting fibrinogen, after depleting fibrinogen, or before depletion of fibrinogen is complete. In some embodiments, the pooling occurs either before or after filtration. In some embodiments, platelets are lysed by thawing either once or multiple times. In some embodiments, a metal salt, such as divalent metal salt, typically a calcium salt, is added to either individual or pooled lysates. In some embodiments, heparin is added to either individual or pooled lysates. In some embodiments, pooled lysate is observed until a visual clot appears. In some embodiments, said visual clot is removed, e.g., by centrifugation.

In some embodiments, the disclosure relates to the product produced by methods disclosed herein. In some embodiments, the product is sterile or substantially free of bacteria, e.g., is mycoplasma negative. In some embodiments, the product has a concentration of fibrinogen of less than 2, 3, 4, 5, 10, 20, or 50 µg/mL. In some embodiments, the product has a concentration of PDGF-BB greater than 1, 5, 10, 15, or 40 ng/mL.

In certain embodiments, disclosure relates to methods of treating or preventing diseases or conditions provided herein comprising administering an effective amount of a pharmaceutical composition comprising fibrinogen depleted platelet lysate or components to a subject in need thereof.

In some embodiments, the disclosure relates to uses as a topical agent and/or the generation of cell products in ophthalmology. In certain embodiments, the disclosure relates to methods of treating or preventing an ocular disease or conditions comprising administering an effective amount of a pharmaceutical composition comprising compositions disclosed herein to a subject in need thereof. In certain embodiments, the subject in need thereof because the subject is diagnosed with, at risk of, or exhibiting symptoms of scleritis, keratitis, corneal ulcer or abrasion, corneal neovascularization, Fuch's dystrophy, keratoconjunctivitis, iritis, uveitis, cataract, chorioretinal inflammation, posterior cyclitis, chorioretinal scars, chorioretinal degeneration, chroriodal dystrophy, choroidal haemorrhage or rupture, choroidal detachment, retinal detachment, retinoschisis, hypertensive retinopathy, diabetic retinopathy, age-related macular degeneration, macular degeneration, retinitis pigmentosa, macular edema, glaucoma, floaters, optic neuropathy, optic disc drusen, amblyopia, scotoma, nyctalopia, red eye, xerophthalmia, or blindness.

In certain embodiments, the disclosure relates to methods of treating or preventing an ocular disease or condition comprising administering an effective amount of composition comprising platelet lysate components disclosed herein to a subject in need thereof.

In certain embodiments, the composition is administered by dropping a solution comprising a composition disclosed herein in the eye of the subject. In certain embodiments, the composition is administered to the interior of the eye, e.g., by syringe or other transfer device such as thin catheter or tub that is inserted through cells of the outer eye in the aqueous humor or vitreous humor.

In certain embodiments, the disclosure contemplates using fibrinogen depleted platelet lysate for generation of immunosuppressive monocytes.

In certain embodiments, the disclosure contemplates using mesenchymal stem/stromal cells generated and disclosed herein to generate in vivo osteoblasts, adipocytes, and chondrocytes, myocytes and neurons.

In certain embodiments, the disclosure relates to compositions comprising platelet lysate components with reduced amounts of fibrinogen compared to platelet lysates produced by a freeze-thaw process, e.g., wherein the composition is substantially depleted of fibrinogen and the platelet lysate components are not substantially depleted of PDGF. In certain embodiment, the composition is an aqueous solution with a concentration of fibrinogen of less than 2 or 4 µg/mL wherein the concentration of PDGF-BB is greater than 15 ng/mL. In certain embodiments, the disclosure relates to compositions made by the processes of removing water from platelet lysate compositions disclosed herein by lyophilization.

In certain embodiments, the disclosure contemplates methods of culturing cells, wherein cells are cultured in a medium comprising platelet lysate components disclosed herein. In certain embodiments, the cells are progenitor cells or stem cells such as pluripotent stem cells, multipotent stem cells, somatic stem cells, mesenchymal stem/stromal cell, adipose-derived stem/stromal cell, endothelial stem cell, dental pulp stem cell, embryonic stem cells, bone marrow or hematopoietic stem cell, amniotic stem cells, lymphoid or myeloid stem cells.

In certain embodiments, the disclosure contemplates methods of treating a wound or wound closure comprising applying a composition comprising platelet lysate compositions or components disclosed herein to the wound. In certain embodiments, the disclosure contemplates wound dressing comprising platelet lysate compositions or components disclosed herein. Examples of wound dressings include bandages, gauze, glues, e.g., cyanoacrylate glues, or sutures. In certain embodiments, the wound dressing further comprises an antibiotic.

DETAILED DESCRIPTION

Figure 1:
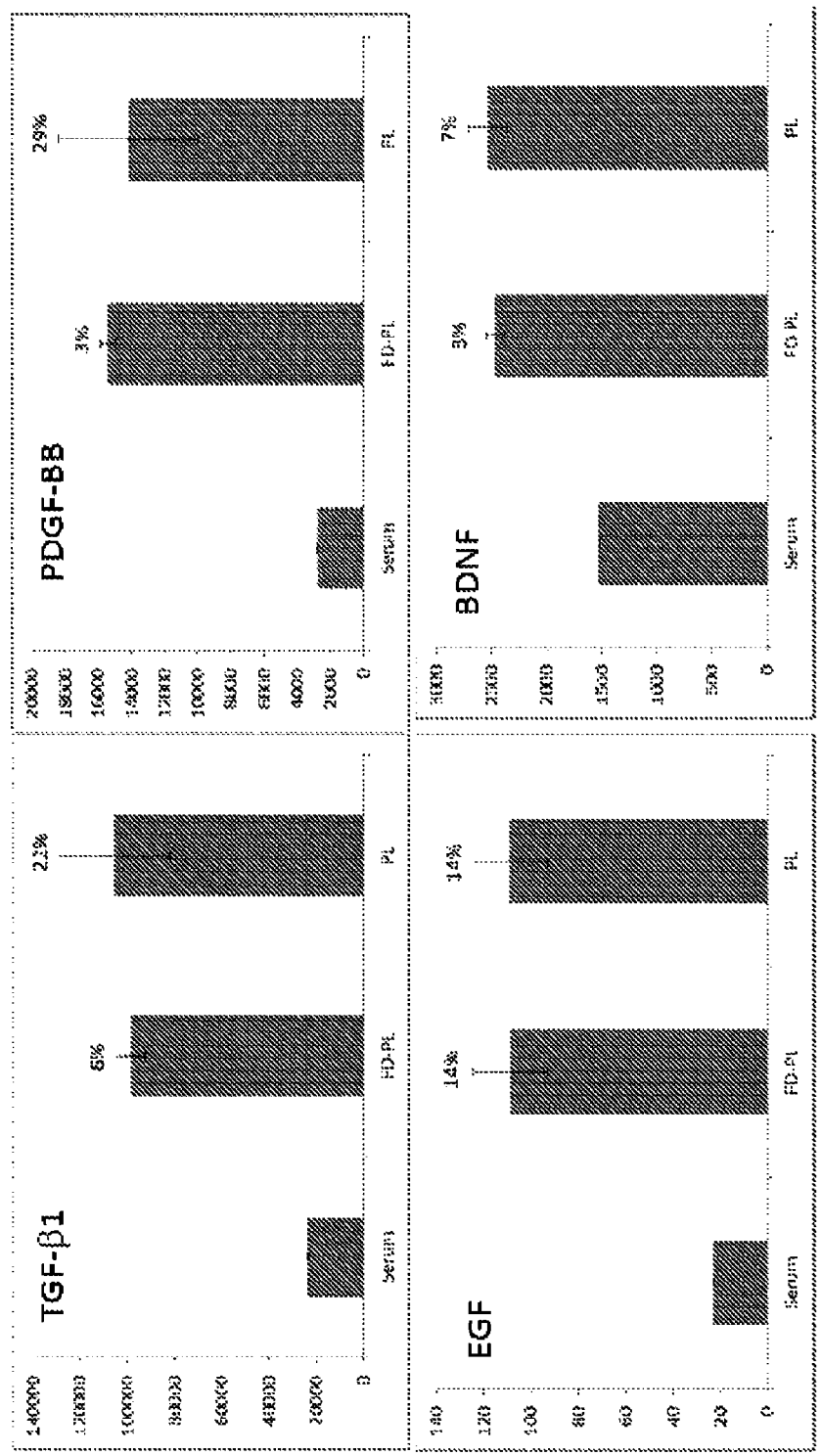
FIG. 1 shows graphical data indicating that despite the reduction in fibrinogen, FD-PL and phPL contain similar levels of desirable growth factors like PDGF, TGF-beta, EGF, and BDNF as measured by ELISA

Depletion of Fibrinogen from Platelet Lysates Using Heparin and Metal Salts

Platelets, or thrombocytes, are cells that do not have a nucleus containing DNA derived from fragmentation of precursor megakaryocytes. Platelets circulate in the blood of mammals and are involved in hemostasis, leading to the formation of blood clots. Plateletpheresis refers to the method of collecting the platelets. Platelets may be pooled from whole-blood or by a device that separates the platelets and returns other portions of the blood to a donor. Serum is typically placed into a large centrifuge in what is referred to as a "soft spin." At these settings, the platelets remain suspended in the plasma. The platelet-rich plasma (PRP) is removed from the RBCs and then centrifuged at a faster setting to harvest the platelets from the plasma. The collected platelets are typically chilled to slow the degradation of the cells.

As used herein the term, the term "platelet lysate" refers to the products of platelet lysis. The platelet lysate may also include any medium in which the lysed platelets are contained. Freezing and thawing is the typical, but not the only, method for lysing cells in this disclosure. Mechanical lysis, typically through the use of shear forces, is another method contemplated for producing a lysate. Lysis buffers, typically acting by placing the cells in a hypotonic solution, are yet another option. The lysis process may consist of combinations of these methods.

In certain embodiments, this disclosure relates to methods wherein heparin and calcium salt are added directly to platelet lysate in order to deplete fibrinogen, re-calcify the lysate, and to neutralize citrate. In another embodiment, the resulting lysate is combined with cell culture media. Previously, heparin was added to cell culture media directly, prior to supplementation with platelet lysate; no evidence of fibrinogen depletion was presented using this prior methodology. See, e.g., Schallmoser et al., Tissue Eng Part C Methods, (2008), 14(3):185-96.

In some embodiments, the disclosure relates to compositions of platelet lysate wherein complement is substantially depleted. This depletion may be achieved by multiple means, as described herein. One use for this depletion is that the embodiments may be used with non-human cells while minimizing the risk of any complement-mediated immune reactivity by human platelet lysate against the non-human cells.

Typically, acid citrate dextrose (ACD) is used as an anti-coagulant. See, e.g., U.S. patent application Ser. No. 12/441,870 (ACD described as "an important blood anticoagulant"). By reducing the availability of calcium, ACD robs the clotting mechanism of the calcium upon which it is dependent. See, e.g., Reich-Slotky et al. J Clin Apher, (2009), 24(6): 265-8. Calcium for use in normal cellular activity is also reduced by ACD, thereby presenting potential toxicity. In this disclosure, heparin is used as the anticoagulant, thereby avoiding the potentially toxic, calcium-depleting effects of ACD. The addition of a salt such as a calcium salt, ideally $CaCl_2$, further neutralizes citrate toxicity and re-calcifies the platelet lysate. In some embodiments, the $CaCl_2$ is dissolved in a buffer, for example Plasmalyte A. In some embodiments, the $CaCl_2$ is dissolved in a sterile, isotonic electrolyte solution at approximately pH 7.4. In certain embodiments, removal of ACD (a calcium chelating anticoagulant) is part of methods disclosed herein. Calcium chelators are deleterious to cell culture and adequate provision of calcium leads to optimal function. Furthermore, heparin-induced stabilization of growth factors and the clarification of the product are results embodied in this disclosure. In certain embodiments, methods disclosed herein do not require the use of ACD.

Fibrinogen depleted platelet lysate (FD-PL or Multiplate FD) compare favorably to unprocessed platelet lysate. Benefits include, but are not limited to, findings that Multiplate FD is superior to unprocessed platelet lysate and FBS in expanding MSCs, Multiplate FD is non-xenogenic (i.e. it poses no risk of zoonosis or prion transmission), Multiplate FD removes the need for additional heparin in culture media, Multiplate FD avoids the risk of fibrous strands forming in media and attaching to MSC monolayer (i.e. decreases risk of micro or macro-occlusions), Multiplate FD is superior with regard to stability to unprocessed platelet lysate in the manufacturing of MSCs for auto and allo-immune therapies, Multiplate FD retains the immunosuppressive characteristics seen using Fetal Bovine Serum and is more versatile than unprocessed platelet lysate for the expansion of cells from multiple lineages and species.

The embodiments described in this disclosure may be applied to clinical treatments for regenerative medicine, immunotherapy, releasing bioactive factors, cancer, and other related fields.

Analysis of Protein Content in Platelet Lysate

Using the RayBio® Human Cytokine Antibody Array C Series 4000 relative expression levels of approximately 174 proteins were compared. Proteins were detected in at least one of the four solutions (human serum, platelet poor plasma, crude platelet lysate (phPL) and fibrinogen depleted platelet lysate (FD-PL)). Of the 116 protein, 87 could be detected in FD-PL, while in phPL 113 proteins were detectable. In serum 67 were detected while in PPP 60 proteins were detected. The most abundant proteins in all samples were typically MSP-alpha, ACRP30, ANGIOGENNIN, and RANTES. Macrophage stimulating protein (MSP-alpha chain) is also known as HGF-like protein (hepatocyte growth factor-like protein) and MST1 (macrophage stimulating 1). It is a 70 kDa disulfide-linked heterodimer (47 and 22 kDa subunits) and when active signals through CD136. Adipocyte complement related protein of 30 kDa (ACRP30) is structurally identical to Adiponectin and is a potent insulin enhancer. Angiogenin is also an abundant plasma protein produced by the liver and has been shown to have both angiogenic and anti-inflammatory properties. Rantes or CCL5 is known mainly for its activity as a chemotactic cytokine but may have a potential role in host defense as a direct antiviral agent. Since each or these proteins can be considered a normal component of plasma there levels were not surprising similar between the various solutions tested. Consequently a ratio analysis was performed between serum vs. PPP, FD-PL vs PPP and phPL vs PPP to determine what factors were released or depleted due to platelets degranulation/clotting or lysis. Six proteins showed increased relative protein expression in FD-PL while 37 proteins were decreased. Of particular interest were the increase in Leptin, PDGF-AA and PDGF-AB levels in FD-PL compared to phPL and a reduction in several MMPs, inflammatory chemokines.

In a separate analysis, normal human serum, platelet poor plasma, crude platelet lysate (phPL) and fibrinogen depleted platelet lysate (FD-PL) was subjected to tryptic digests and analyzed for protein expression using Mass Spectrometry. Apolipoproteins were the most highly represented family of proteins detected (N=3) followed by members of the complement cascade (N=6). Confirming our ELISA data, MS-analysis showed that the manufacturing protocol of platelet lysate depletes fibrinogen. In FD-PL, fibrinogen levels are at least 10 fold reduced compared to phPL resembling serum levels more than platelet poor plasma. The manufacturing protocol also selectively depletes complement 4, Complement C1s subcomponent, and complement factor B, which are retained in phPL and PPP. Compared to both serum and PPP, platelet lysates (phPL and FD-PL) contain detectable levels of several cytoskeletal and cytoskeletal associated proteins like Actin, Filamin, Talin, and Zyxin. Both PLs contain detectable levels of Thymosin beta 4 with FD-PL having approximately twice the amount of ThB4 of phPL. Further FD-PL is depleted of factors including, Hemopexin, Apolipoprotein CIII, Apolipoprotein AI Alpha-2-macroglobulin and Alpha-1B-glycoprotein, but enhanced for Alpha-2-HS-glycoprotein, Apoliproprotein L1, Clusterin/Apolipoprotein J and Platelet basic protein.

In addition to the depletion of complement and MMP, Fibrogen and fibrin depletion enhances the safety FD-PL product. Fibrinogen is converted to fibrin. Fibrin and has reported to induce inflammation. See Rowland et al., Curr Eye Res. 1985, 4(5):537-53. Fibrin can cause CEC to produce IL-8. See Ramsby et al., Invest Ophthalmol Vis Sci. 1994, 35(12):3980-90 and Drew et al., Invest Ophthalmol Vis Sci. 2000, 41(1):67-72.). Furthermore fibrinogen can directly signal on Monocytes via TLR4 to increase MCP-1 MIP-1alpha, MIP-1beta and MIP-2. See Smiley et al., J Immunol 2001, 167(5):2887-94 and Sitrin et al., J Immunol 161:1462-1470, 1998. It can prolong the inflammatory response of neutrophils by binding to the α-subunit of CD11b/CD18 on the surface of neutrophils and thereby activating the Erk signaling pathway. See Rubel et al. J Immunol 166:2002-2010, 2001. Finally it has been shown that adsorbed fibrinogen is the primary component of plasma responsible for acute inflammatory responses to many implanted materials. See Tang et al., J Exp Med 178:2147-2156, 1993. Thus depletion of fibrinogen from our platelet lysate reduces the chance of this product adversely affecting cells (like MSCs which express TLR4) in culture and creates a better safety profile for the direct topical application of this product to patients.

Therapeutic Indications

In certain embodiments, the disclosure contemplates that fibrinogen depleted platelet lystate compositions contained herein may be used directly or depleted of water by process such as lyophilization, i.e., freeze drying, to provided dehydrated products that may be added to cell cultures and pharmaceutically acceptable excipients and used in therapeutic applications provided herein.

Dry eye is a major complication associated with chronic graft-versus-host disease after hematopoietic stem cell transplantation. Pezzotta et al., Bone Marrow Transplant, 2012, doi: 10.1038/bmt.2012.64, reported that autologous platelet lysate may be used for the treatment of ocular GvHD. In certain embodiments, this disclosure relates to the treatment of dry eye comprising administering an effective amount of a fibrinogen depleted platelet lysate composition disclosed herein to the eye of a subject.

Sandri et al., Int J Pharm, 2012, 426(1-2):1-6 report that eyedrops containing platelet lysate are useful for the treatment of corneal ulcers. In certain embodiments, this disclosure relates to the treatment of corneal diseases or conditions comprising administering an effective amount of a fibrinogen depleted platelet lysate composition disclosed herein to the eye of a subject.

FD-PL and phPL have a number of similarities, but because of our manufacturing procedure there is a selective depletion and accumulation of a number of proteins which make FD-PL a distinct product. Of particular interest is the fact that FD-PL has increased amounts of TB4 a factor that has angiogenic, pro-survival and anti-inflammatory properties and is currently being evaluated clinical for ocular tissue regeneration.

Ranzato et al., J Cell Mol Med, 2009, 13(8B):2030-8, report that platelet lysates promote wound scratch closure of human fibroblasts. In certain embodiments, this disclosure relates to the use of fibrinogen depleted platelet lysate compositions or components for wound healing applications. In certain embodiments, the disclosure relates to methods of treating wounds comprising administering or applying a composition comprising fibrinogen depleted platelet lysate components to the subject or on an area of the subject with a wound. The pharmaceutical composition may be in the form of a lotion or oil or aqueous solution containing fibrinogen depleted platelet lysate compositions.

Terms

As used herein, the term "cell culture medium" refers to any medium capable of supporting the in vitro proliferation of mammalian cells. Typically, this will comprise an isotonic solution at approximately pH 7.4 containing amino acids, one or more antibiotics, vitamins, salts, and glucose. Examples of media containing some or all of these criteria include, but are not limited to, DMEM and RPMI.

As used herein, the term "heparin" refers to any variety of sulfated polysaccharides, fragments and derivatives that have anti-coagulant properties. Typically, heparins compositions are a mixture with a range of molecular weights from about 3 kDa to about 30 kDa. Heparin binds to the enzyme inhibitor anti-thrombin (AT). When bound, AT undergoes a conformation change and is activated. The activated AT is capable of inactivating thrombin and other proteases. This prevents thrombin from converting fibrinogen to fibrin, thereby disrupting the clotting process.

As used herein, the term "MSC" refers to a mesenchymal stem cell, otherwise known as a mesenchymal stromal cell. A human MCS is typically identified by surface markers including CD29, CD44, CD45, CD51, CD71, CD73, CD90, CD105, CD106, and CD166. MSCs are pluripotent cells that may be obtained from multiple locations within the body, such as from bone marrow, adipose tissue, or blood. MSCs are the typical, but not the only, cell type to be proliferated using the embodiments described in this disclosure.

As used herein, the term "PDGF" refers to a platelet-derived growth factor. In human platelet lysate, there are multiple types of PDGF (Gen Bank Accession AAA60552.1), including PDGF-AB, PDGF-AA, and PDGF-BB (Gen Bank Accession CAA45383.1). All three PDGF isoforms bind to PDGFRα, whereas PDGF-AB and PDGF-BB bind to PDGFRβ. Both PDGFRs are tyrosine kinase receptors. PDGFRs are phosphorylated once bound by PDGF. This in turn stimulates kinase catalytic activity as well as the formation of binding sites for SH2-containing downstream signaling molecules. See Heldin et al., Mechanism of action and in vivo role of platelet-derived growth factor, Physiol Rev, (1999), October; 79(4):1283-316. The binding of PDGF to PDGFRs can induce numerous biological effects. PDGF has a wide variety of biological functions. PDGF is critical to embryonic development, is involved in the development of the central nervous system, maintains interstitial fluid pressure, has an angiogenic effect on the vascular system, and has been shown to increase the rate of wound healing. In vitro, PDGF, as a component of human platelet lysate, has been shown to be a viable alternative to FBS for proliferating cells, in particular MSCs. See, e.g., Horn et al., Impact of individual platelet lysates on isolation and growth of human mesenchymal stromal cells, Cytotherapy, (2010), 12(7):888-98. The term PDGF is not intended to be limited to any particular sequence provided there is sufficient sequence homology and functional attributes.

EXPERIMENTAL

Example 1: Manufacturing of PL for Recovery and Fibrinogen Depletion

Approximately 10% volume of citrate which acts as a calcium chelator is added to plateletpheresis products (phPL) to prevent inadvertent clotting of the product prior to patient infusions. Inserting a re-calcification step into the phPL manufacturing process was tested to evaluate whether a more stable and uniform product is produced. As such several concentrations of calcium chloride and incubation times were evaluated.

During these studies the following conditions were evaluated.

1. PL+5 mM $CaCl_2$, RT (1 12 hours)
2. PL+5 mM $CaCl_2$, 37 C (1-12 hours)
3. PL+10 mM $CaCl_2$, RT (1-12 hours)
4. PL+10 mM $CaCl_2$, 37 C (1-12 hours)
5. PL+16 mM $CaCl_2$, RT (1-12 hours)
6. PL+16 mM $CaCl_2$, 37 C (1-12 hours)
7. PL+20 mM $CaCl_2$, RT (1-12 hours)
8. PL+20 mM $CaCl_2$, 37 C (1-12 hours)

Data from these studies demonstrated that 5 mM $CaCl_2$ was incapable of forming a clot at either temperature. 12 hours of 10 mM $CaCl_2$ at 37 C was capable of forming a clot however this clot almost completely solidified allowing for very little recovery of supernates. The higher concentrations of $CaCl_2$ also generally formed completely rigid clots if allowed to incubate for more than 1 hour. In subsequent experiments, $CaCl_2$ concentrations were evaluated between 6-10 mM. If clotting occurred, it generally occurred quickly and was complete. Furthermore there was variability between batches at to what concentration of $CaCl_2$ was necessary to initiate clot formation.

To further refine this process 1) heparin was add at a concentration of 2 U/mL to control the clotting procedure 2) $CaCl_2$ was dissolved in plasmalyte vs water to increase stability 3) a double freeze thaw was performed to increase platelet membrane lysis, 4) the clot was allowed form for 1 hour at RT or 37 then overnight a 4 C. Upon dilution of unmodified phPL into cell culture media the calcium present in the basal media is sufficient to overwhelm the citrate chelating capacity which allows the conversion of free fibrinogen to fibrin which can then amalgamate to form a clot.

Groups 5-8 from our first experiments were used. All groups showed a certain degree of clot formation and incubation of the solutions overnight at 4 degree allowed the clot to stabilize. Compared to our first experiments, the changes implemented allowed us to spin the solution the next day and recover the majority of the solutions (i.e. 70-80%) whereas in the first experiments at higher $CaCl_2$ concentrations our recovery was closer to 20%. By adding heparin to the solution there was some residual fibrinogen remaining, however this was not sufficient to cause subsequent gel formation to occur. It became evident that using a double freeze thaw resulted in release of growth factors like PDGF-BB. Based upon these experiments, a double freeze thaw procedure was followed by requalification with 20 mM $CaCl_2$ in the presence of 2 U/mL heparin. This process was subsequently preformed in a number of manufacturing runs to establish consistency. FD-PL product could be reliably produced such that fibrinogen content was less than 4 ug/ml with approximate 12% variability between batches. Unprocessed phPL typically had fibrinogen content of 60 µg/mL. Of particular interest is the fact that despite the reduction in fibrinogen, FD-PL and phPL contain similar levels of desirable growth factors like PDGF, TGF-beta, EGF, and BDNF as measured by ELISA. See FIG. 1.

A typical GMP preparation of FD-PL (Multiplate FD) from frozen human plateletpheresis products is provided below. Approximately five human donor retested outdated plateletpheresis products were removed from a freezer and thawed overnight at 4° C. The samples were next transferred to a class 10,000 cGMP clean room for refreezing at −20° C. Small aliquots from each sample were taken for microbiological testing. Samples with aliquots free of contamination were then thawed overnight at 4° C. Samples were next centrifuged at 4000 rpm for 15 minutes in order to pellet cell debris using a COBE Cell processor. Supernatants from each sample were then passed through 40 µm filter and then pooled together. This pooled sample filtrate was then placed in 250 mL centrifuge tubes for centrifugation at 3000 g for 15 min at 4° C. to pellet any remaining debris. The resulting pooled sample supernatant was then given an eight digit ID based on the date (e.g. Dec. 13, 2010=13122011). 16-20 mM $CaCl_2$ (dissolved in Plasmalyte A) was then added to re-calcify and neutralize citrate content in the sample. 1.5-2.5 Units/mL heparin (1000 units/mL stock) was then added to the sample to modulate this process. The sample was kept at 37° C.+/−2° C. for 2-4 hours until a visual clot appeared. The sample was then placed at 4° C. for 16-24 h until the clot size stabilized. The sample was centrifuged for 15 min at 3000 g. The sample was then clarified via 0.2 um filtration. The sample was then stored at either 4° C. or frozen as low as −80±10° C. If frozen, a small aliquot of pooled sample was taken for mycoplasma sterility testing and fibrinogen/PDGF quantification. The sample was approved if mycoplasma detection was negative, the fibrinogen concentration was less than 2 µg/mL, and the PDGF-BB concentration was greater than 15 ng/mL.

Example 2: Optimal Reduction of Fibrinogen Levels does not Significantly Alter Biochemical or Growth Factor, Cytokine or Chemokine Thawed platelet units were individually filtered through a 40 µm PALL blood transfusion filter (PALL BIOMEDICAL, INC Fajardo, PR) and allowed to pool into a collection bag. Pooled, filtered lysate was equally aliquoted into labeled 250 ml conical tubes (Corning® Lowell, Mass. USA) and spun for 20 minutes at 4600 rpm in room temperature. Spun lysate was again filtered (40 µm), aliquoted into new labeled 250 mL conical tubes, and progressively filter to 0.2 µm (unmodified PL). Aliquots of unmodified platelet lysate was then combined with various concentrations of CaCl$_2$ and incubated for various times at specific temperatures. A preferred formulation was found to be a double freeze thaw of the platelet units followed by re-calcification to 20 mM CaCl$_2$ in combination with 2 U/ml heparin sulphate follow by incubation at 37° C.+/−2° C. for 2 hours to allow a clot to form. This was followed by a 16 hour incubation at 4° C. to allow clot size stabilized. This procedure allowed for a greater than 150 fold reduction of fibrinogen, with an interbatch variability of approximately 10%. Biochemically the addition of CaCl$_2$ to Multiplate FD cause osmolarity and calcium and chloride concentrations to be higher than those of unprocessed platelet lysate, however numerous other factors namely, Na, K, glucose, total protein and albumin levels were not significantly different between unmodified PL and Multiplate FD.

|  | Serum | PPP | FD-PL | PL |
| --- | --- | --- | --- | --- |
| Osmolarity | 301 | 311 | 350 | 309 |
| NA | 140 | 141 | 154 | 160 |
| K | 4.1 | >15 | 5 | 5 |
| CL | 105 | 100 | 123 | 85 |
| Glu | 92 | 101 | 217 | 247 |
| Bun | 11 | 12 | 12 | 14 |
| Creat | 0.94 | 1.04 | 1 | 1 |
| CO | 279 | 282 | 313 | 326 |
| TPROT | 7.1 | 7.1 | 5 | 5 |
| ALB | 4.6 | 4.5 | 3 | 3 |
| CA | 9.6 | <2.0 | >20 | 6 |
| AP | 45 | <5 | 47 | 41 |
| AST | 30 | 30 | 36 | 42 |

Platelet lysate differs from both serum and plasma in that it contains not only normal platelet degranulation release products but also intracellular components not normally released. Furthermore platelet lysate contains a much higher concentration of platelets compared to normal plasma or serum and thus the concentration of release factors is considerable higher. To garner a broad overview of the cytokines and growth factors prevalent in platelet poor plasma (PPP), Serum and platelet lysate and Multiplate FD were employed in a protein array screening technology. The technology is based on the sandwich immunoassay principle. A panel of antibodies (capture) was immobilized at specific spot locations on the surface of a membrane. Incubation of array membranes with biological samples results in the capture of cytokines by corresponding antibodies. The bound cytokines are detected with a cocktail of biotinylated antibodies. Signals are then visualized using chemiluminescence. Using the RayBio® Human Cytokine Antibody Array C4000 allowed us to simultaneously detect 174 cytokines. According to the manufactures protocol, membranes were incubated with equivalent amount of total protein for PPP, Serum or platelet lysate and Multiplate FD diluted in α-MEM media.

Using these arrays, some proteins were similarly expressed between the groups; however in some instances platelet lysate and Multiplate FD showed higher expression for several proteins. Of particular interest are the elevated levels of proteins like all three PDGF isoforms, EGF, and BDNF as well as protease inhibitors like TIMP-1 and PAI-1 found in PL versus serum and PPP. Confirming array data, PDGF-BB, EGF, BNDF, TGF-b1 and VEGF levels were analyzed in PPP, Serum, platelet lysate and Multiplate FD. Compared to both PPP and serum, Multiplate FD and platelet lysate phPL had increase concentrations for each cytokine. On average (N=3 batches) there was no statistical difference between EGF, PDGF-BB, TGF-b1 or BDNF levels between Multiplate FD and PL, however interbatch variability in with regards to PDGF-BB and TGF-b1 levels were lower in Multiplate FD compared to PL. Depletion of fibrinogen from platelet lysate results in a more reliable product with regards to consistency.

Example 3: Multiplate FD is More Stable than Unprocessed Platelet Lysate (phPL)

Strategies for using phPL as a growth supplement for MSCs are reported. However cultures employing phPL as a growth supplement include the addition of heparin (usually 2 U/ml) to prevent fibrin gel formation. In working with non-fibrinogen depleted platelet lysate (phPL), it was observed that once manufactured and filtered to 0.2 μm the solution is optically clear and does not contain noticeable debris, however upon freezing and re-thawing or upon storage at 4° C. new precipitate forms in this phPL. This accumulates over time making the solution turbid which cannot be removed by centrifugation alone, typically requiring re-filtration. Therefore in order to garner a better idea of whether FD-PL was susceptible to a similar precipitate accumulation, phPL and FD-PL were manufacture from the same pool of plateletpheresis. The products were frozen at −30° C. until use. Aliquots of phPL and FD-PL were then thawed at 4° C. overnight, centrifuged at 3000×g for 10 minutes to remove cryopreciptate and filtered to 0.2 μm and particle analysis performed either immediately or after storage at 4° C. for 24 hours or 7 days.

Figure 2:
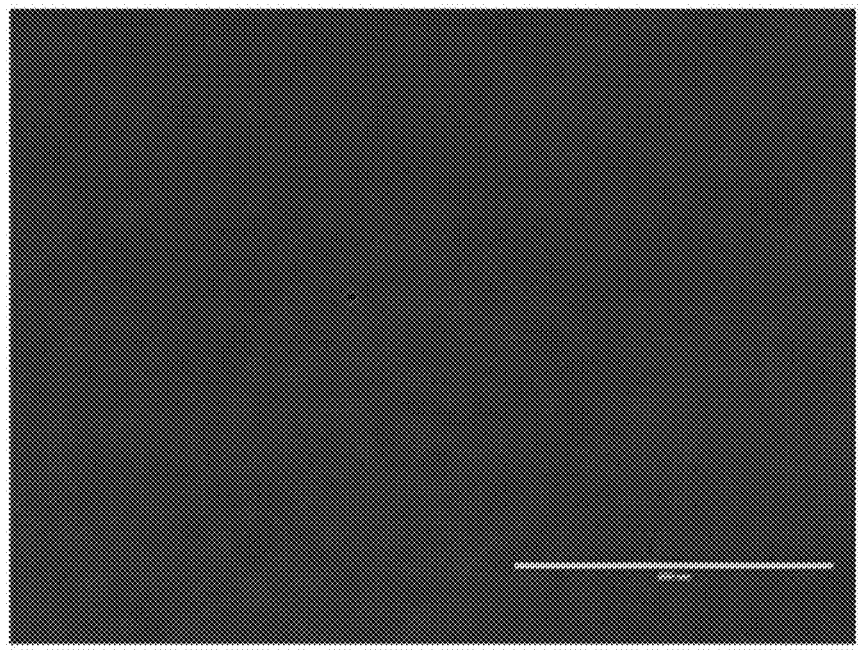
FIG. 2 shows microscopic analysis after 7 days of storage indicating FD-PL (top) is essentially free of debris whereas phPL (bottom) contains particles of varying size.
Figure 2:
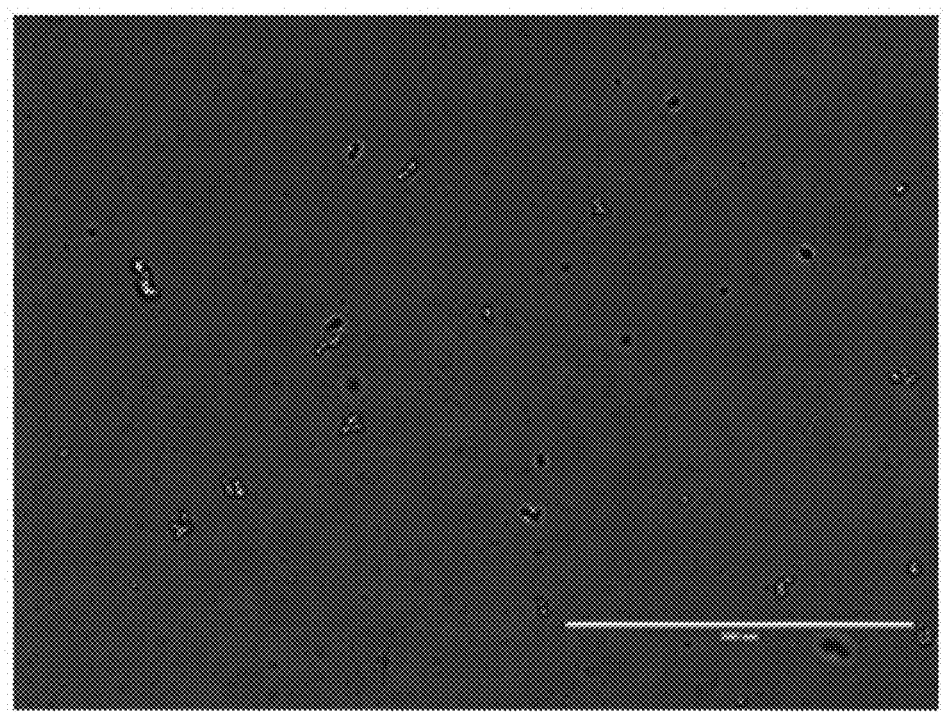

Particle analysis was performed on phPL and FD-PL using a Beckmann Coulter Canto II flow cytometer using Forward and Side Scatter signals to estimate particle size, abundance and granularity. Laser power for FSC and SSC were set to logarithmic scale and set to ensure particles of all sized would be recorded. To obtain a relative quantification of particles data acquisition collection was set for each sample for exactly 15 seconds. Immediately following filtration both phPL and FD-PL had small amount of debris detected which did not noticeable change in FD-PL over time. Conversely even after 24 hours of filtration phPL showed an increase in particle numbers and size, which continued outwards at 7 days. Microscopic analysis could demonstrate a similar observation such that at 7 days FD-PL was essentially free of debris whereas phPL contains particles of varying size. See FIG. 2. Using the disclosed manufacturing process one can generate a platelet lysate product that contains significantly less debris and more stable.

Following the manufacturing of unprocessed and Multiplate FD from the same 5 donor pool of plateletpheresis product aliquots were frozen at −80° C. for 1 month. Subsequently aliquots were thawed overnight at 4° C. spun at 3000 xg to remove cryopreciptate and then progressively filtered to 0.2 mm Following filtration undiluted or diluted (20% in Plasmalyte A) platelet lysate and Multiplate were immediately analyzed by flow cytometry for debris then stored at 4° C. and subsequently analyzed each day for 4 days Immediately after filtration both platelet lysate and Multiplate FD has similar amount of debris in both the undiluted and diluted samples, however by 24 hours there was a significant and progressive accumulation of debris formation in the platelet lysate in compared to Multiplate FD. Consistent with our flow cytometry analysis visualization of the debris accumulation demonstrates that in Multiplate FD the accumulation of debris is dramatically less than platelet lysate and significantly smaller. In platelet lysate debris appears to aggregate overtime and by day 3 these aggregates can reach sizes in the realm of 5-10 µm, while the debris does not appear to aggregate and is generally smaller than 2 µm.

Example 4: Multiplate FD Achieves a Superior Rate of MSC Proliferation to FBS, and Unprocessed Platelet Lysate, and Maintains Immunophenotype and Immunosuppressive Properties Autologous and allogeneic MSCs have been reported for treating conditions involving both ischemia and immune dysregulation. The majority of ex vivo cell manipulations have relied on fetal bovine serum (FBS) to propagate MSCs in adherent cultures. Since FBS is xenogeneic, cells exposed to it have the potential to become immunogenic, and it has been reported that repeated administration of cells cultured with FBS can elicit adverse reactions in patients. To this end, MSCs have been cultured in human-derived alternatives to FBS including human serum and platelet-rich plasma. It has been reported that replacing FBS with human platelet-derived growth factors (in the form of human platelet lysate, hPL) can promote MSC growth.

Figure 3:
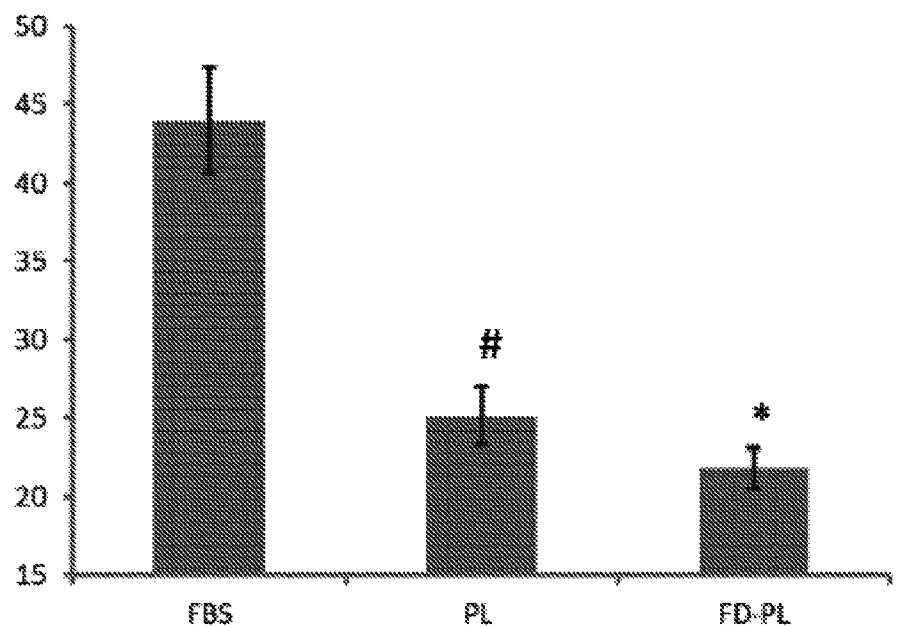
FIG. 3 shows data where MSCs are ex vivo expanded in FBS, phPL and FD-PL demonstrating that culturing MSCs in FD-PL can significantly shorten doubling time compared to both FBS and phPL.

To evaluate whether functionality as a growth supplement is retained in FD-PL, a series of in vitro experiments were conducted to compare FD-PL product to phPL. Primary cells were tested from the mesenchymal lineage, endothelial and epithelial lineage. Mesenchymal cell were isolated from the bone marrow of healthy volunteers and expanded until passage. After passage, two mesenchymal stromal cell preparations were seeded at 1000 cell/cm$^2$ in tissue culture flasks containing media with FBS, phPL or FD-PL. MSCs were then allowed to grow for 3 days, harvested, and the cell numbers counted. Population doubling time was then calculated. Both phPL and FD-PL could significantly reduce doubling time. When directly compared to one another, MSC expanded in FD-PL had a lower doubling time compared to MSCs in phPL (FIG. 3). Phenotypically, MSCs grown in either FBS, phPL or FD-PL all expressed the typically markers of MSCs including: CD44, CD90, CD73, HLA-I, CD105 and did not show expression of CD45, CD11b, CD34 or CD19. These experiments indicate that MSCs grow faster in FD-PL compared to both FBS and phPL, and it does not adversely affect their immunophenotype MSCs have been reported to effect T cell activation and proliferation in vitro. One mechanism by which MSCs are proposed to influence T-cell proliferation is via Indoleamine 2,3-dioxygenase (IDO). IDO is an immunomodulatory enzyme that catalyzes the degradation of the essential amino acid L-tryptophan to N-formylkynurenine. IDO is the first and rate-limiting enzyme of tryptophan catabolism through kynurenine pathway. Depletion of local tryptophan has been shown to halt the growth of T cells. Un-stimulated MSCs do not express IDO, however IDO gene expression is rapidly increased by inflammatory cytokines like INF-γ. The ability of MSCs to up-regulate IDO expression is correlated to their ability to suppress T-cell proliferation.

Figure 4:
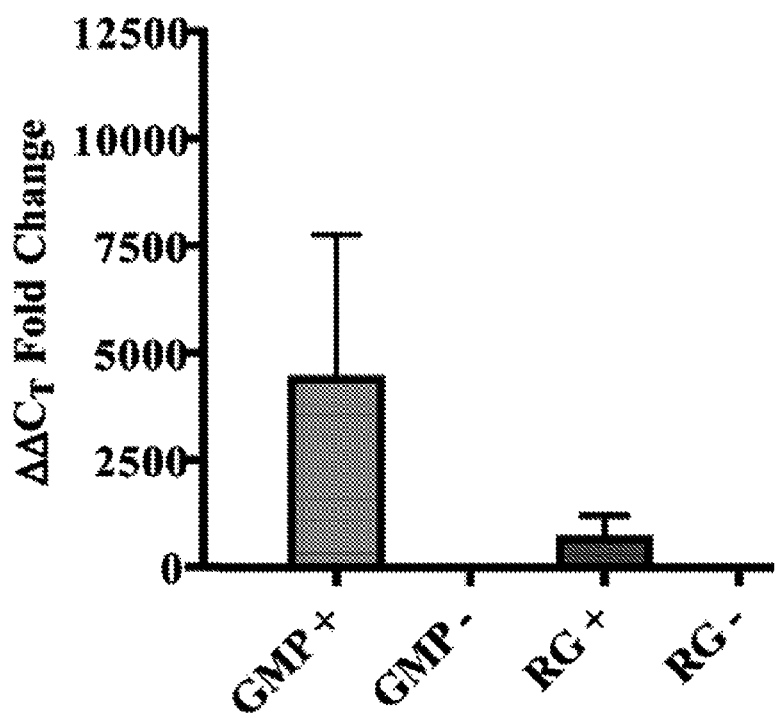
FIG. 4 shows data on the INF-gamma responsiveness of MSCs based on IDO induction when cultured in from FD-PL (GMP) and phPL (RG) indicating that FD-PL expanded MSCs have superior immunosuppressive potential.

To evaluate whether MSCs grown in either phPL or FD-PL influences their ability to up-regulate IDO to inflammatory stimuli bone marrow derived MSC populations were propagated in phPL or FD-PL for 2 passages (i.e. 2 weeks). Each population was seeded into 6 well plates at a density of 100,000 cells/well overnight. The following day, MSCs were either stimulated with 5 ng/ml INF-γ or left unstimulated in their respective media for 4 hours. Cells were washed and lysised in RLT buffer with b-mercaptoethanol and store at −80° C. until the RNA was extracted. DNA-free total RNA was extracted and reverse transcribed as described. Real-time qPCR assays were performed in duplicate on an ABI 7500 Fast Real-Time PCR system thermal cycler and SYBR Green Mastermix (Applied Biosystems) with human primers sequence (5'3' forward, reverse) for IDO and b-actin (house keeping gene). Real-time PCR analysis demonstrated that unstimulated MSCs grown in either phPL or FD-PL do not have substantial amounts of IDO gene expression however 4 hours of stimulation with INF-γ sufficient to increase IDO expression in MSCs in both media. See FIG. 4.

Example 5: FD-PL Suppresses T-Cell Proliferation Ex Vivo

ConA is a lectin that binds to and non-specifically activates T cells. PHA and PMA are phorbol ester compounds that can activate multiple proliferative signaling pathways in cells. A CD3/CD28 stimulation protocol was utilized which is specific to T-cells. Using CD3/CD28 stimulation of peripheral blood mononuclear cells (PBMCs) labeled with the fluorescent marker CFSE, one can track the proliferation of T-cell based using flow cytometry based on the relative decrease in signal intensity and then assess whether a treatment impact the proliferation of activated T-cells.

In performing the PBMC proliferation assays with or without MSCs, it was observed that when PBMCs alone were cultured in RPMI 10% with FBS and stimulated with CD3/CD28 beads, T-cells vigorously proliferated, however when FBS was replaced with FD-PL stimulated PBMCs did not proliferate. Analysis of three separate experiments reveals that compared to serum, FD-PL was able to suppress a T-cell proliferative response in stimulated PBMCs by 4.7 fold compared to FBS.

Figure 5:
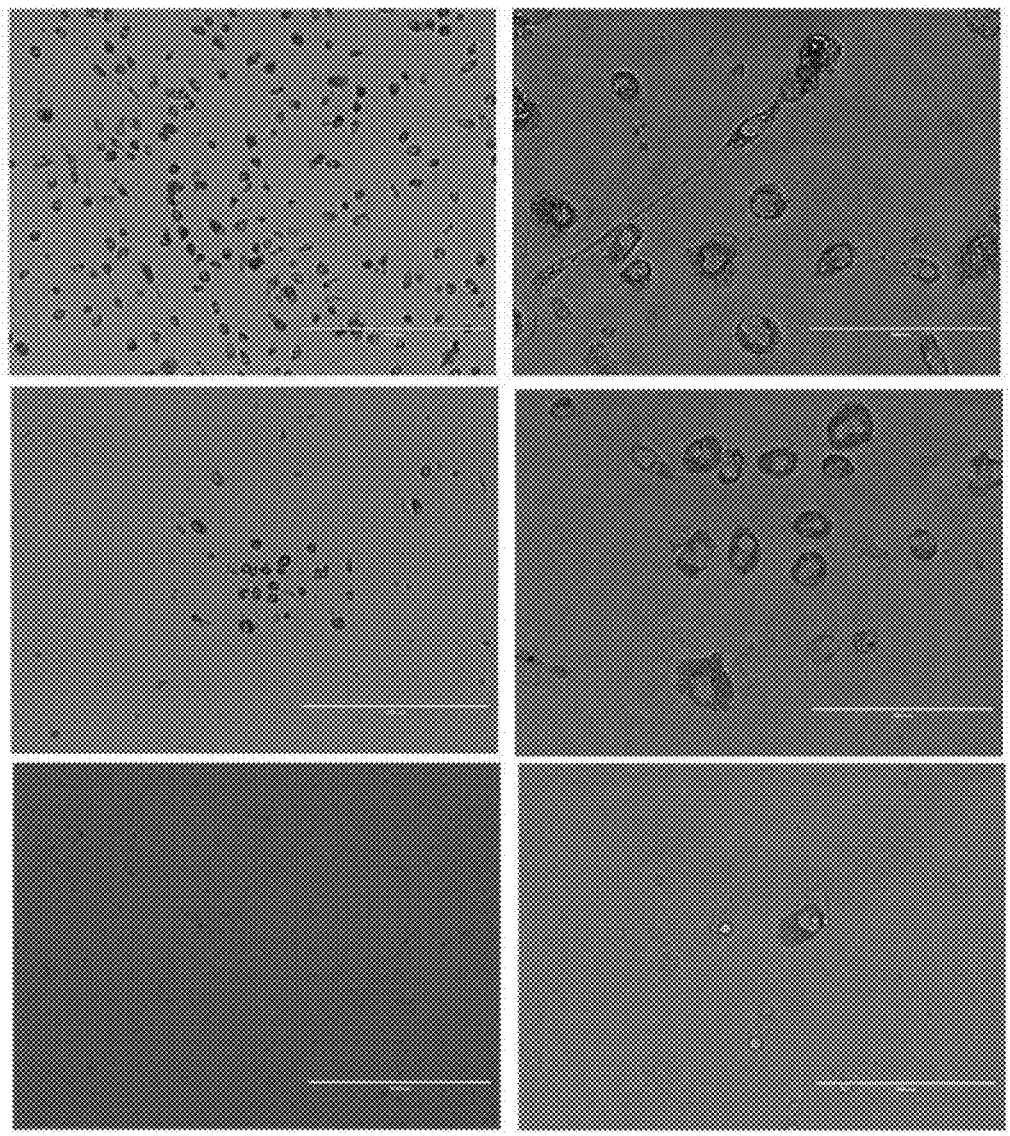
FIG. 5 shows microscopic analysis (right expanded view of left) of FD-PL (top), phPL (middle), and serum (bottom) indicating FD-PL is capable of promoting the attachment and expansion of a CD11b and CD33 positive monocyte populations.

As PBMC responder cells represent a heterogeneous mixture of lymphomyeloid cells including lymphocytes and monocytes (typically in a 4:1 ratio), a subsequent series of experiments was conducted to determine if FD-PL acted directly on T-cells or monocytes. Using immunomagnetic separation we performed negative selection to derive a population of highly purified T-cells and monocytes to compare with unfractionated PBMCs. When PBMCs alone were stimulated in Serum, T-cells underwent robust proliferation, while in phPL proliferation was blunted. To our surprise, when T-cells alone were stimulated proliferation occurred in both Serum and phPL cultures. Thus implies that FD-PL does not directly inhibit to T-cell proliferation. Confirming this hypothesis add back experiments were performed and indicated that supplementing T-cells with specific concentrations of monocytes could dose dependently reduce T-cell proliferation in in the phPL conditions. Subsequently a series of experiments were performed using unlabeled PBMCs cultured for 3-days in either Serum, phPL or FD-PL (10% concentration) and found FD-PL alone is capable of promoting the attachment and expansion of a CD11b and CD33 positive monocyte population that is CD14 negative which cannot be readily generated using serum or phPL. See FIG. 5. Thus FD-PL has robust anti-inflammatory properties in vitro through unique actions on monocytes.

Example 6: FD-PL is More Versatile for the Ex Vivo Culturing Multiple Cell Types Frozen primary human corneal epithelial cells (HCEC) from Life technologies were expanded them their optimized media and growth supplement cocktail for one passage. Upon subculturing HCEC were placed into various conditions to determine whether serum, phPL or FD-PL could replace the optimized growth supplement cocktail. HCEC were plated at 50,000 cells/well in 6 well plates in media containing a) Optimal media+Optimal Growth factor cocktail
b) Optimal media+Allogeneic Serum at 1, 5 & 10% concentration.
c) Optimal media+Allogeneic phPL at 1, 5, & 10% concentration.
d) Optimal media+Allogeneic FD-PL at 1, 5, & 10% concentration.

Figure 6:
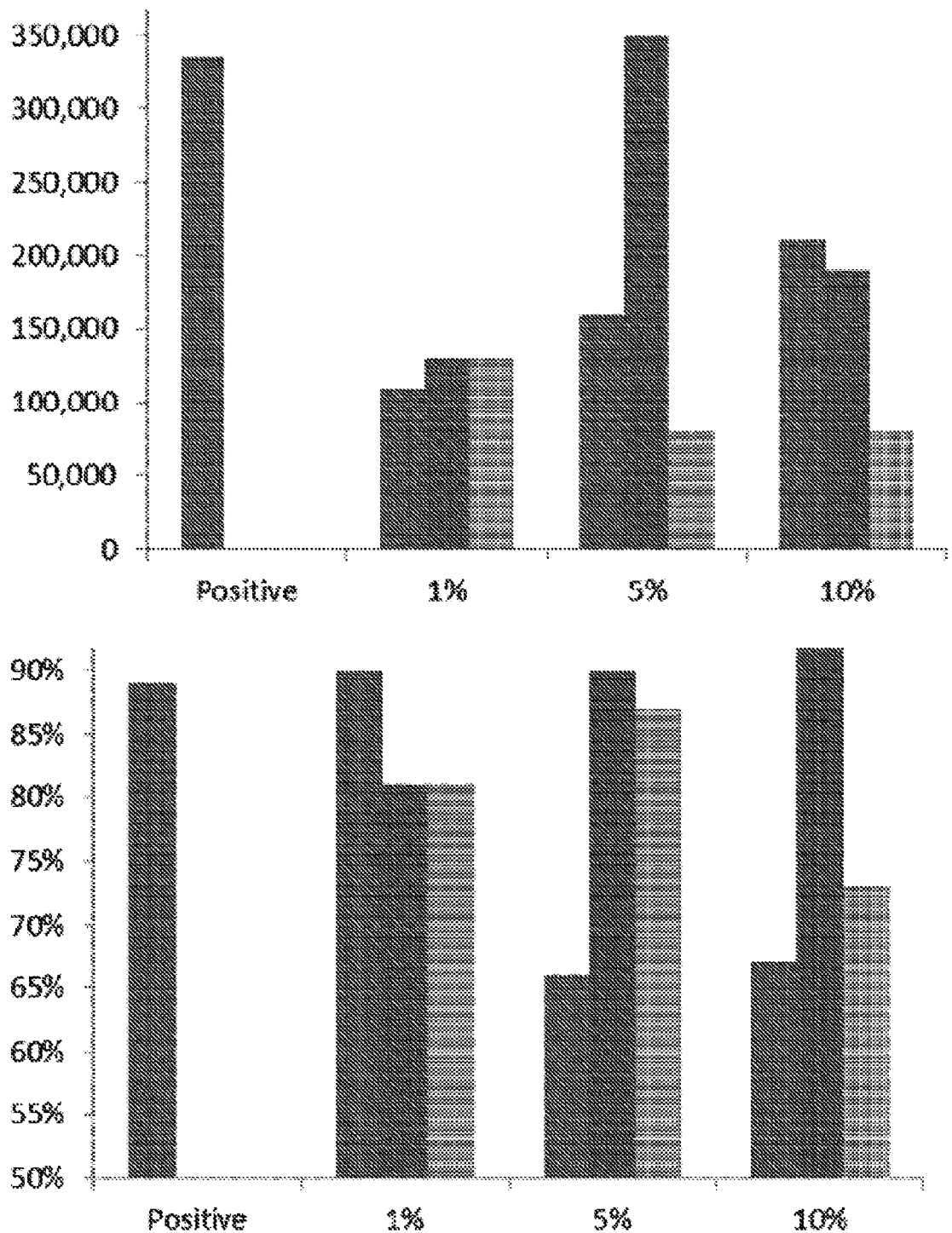
FIG. 6 shows data on the proliferation (top) and viability (bottom) of using phPL (left), FD-PL (middle), and serum (right) growing Human Corneal Epithelial Cells (HCEC).

After three days in culture the HCECs were collected for each condition analyzed for cell number and viability. See FIG. 6. The results demonstrated that increasing concentration of FD-PL enhanced the viability HCECs and at increasing concentration could produce a dose dependent proliferative response. The proliferative response on HCECs was maximal at a 5% concentration and was equivalent to the commercially available growth factor cocktail. Conversely both serum and crude PL reduced viability with increasing concentration and regardless of concentration were incapable of producing a proliferative response that was comparable to commercially available growth factor cocktail. Thus FD-PL showed and enhance toxicology profile and functional usage in epithelial cells compared to either serum or phPL.

MSCs were cultured in media containing 10% (v/v) FBS, unmodified platelet lysate, or FD-PL. 2 units/mL of heparin were added to the media containing unprocessed platelet lysate in order to prevent conversion of fibrinogen to fibrin. Proliferation of MSCs in both unprocessed platelet lysate and FD-PL groups was superior to the MSC proliferation in the FBS group. Following 72 hours Various cell types were cultured in media containing either FD-PL or phPL. Both FD-PL and phPL were capable of growing MSCs from human, porcine and primate origin. FD-PL was also superior to serum and phPL in the ex vivo generation of immunosuppressive monocytes-derived cells from unfractionated peripheral blood mononuclear cells. FD-PL was also capable of propagating 4T1, NIH 3T3 cells, human corneal epithelial cells and human endothelial cells, whereas phPL did not promote the expansion or survival of these cells.

What we claim:

1. A composition comprising heparin, heparin-stabilized growth factors and components from a lysate of platelet-pheresis products, wherein the composition comprises a concentration of fibrinogen of less than 50 μg/ml and a concentration of PDGF-BB greater than 10 ng/mL.

2. The composition of claim 1, wherein the composition is substantially depleted of fibrinogen.

3. The composition of claim 1, wherein the platelet lysate components are not substantially depleted of PDGF.

4. The composition of claim 1, wherein the composition is an aqueous solution.

5. The composition of claim 4, wherein the concentration of fibrinogen is less than 4 μg/mL.

6. The composition of claim 1, wherein the concentration of fibrinogen is less than 10 μg/ml.

7. The composition of claim 1, wherein the concentration of fibrinogen is less than 2 μg/ml.

8. The composition of claim 1, wherein the composition is substantially free of cryoprecipitate.

9. The composition of claim 1, further comprising cell culture medium components.

10. The composition of claim 1, wherein the composition is substantially free of cell debris.

11. The composition of claim 1, further comprising a calcium salt.

12. The composition of claim 11, wherein the calcium salt is dissolved in a buffer or an isotonic electrolyte solution.

13. The composition of claim 11, wherein the calcium salt is calcium chloride.

14. A composition made by the processes of removing water from a composition of claim 4.

15. A method of culturing cells, wherein cells are cultured in a medium comprising the composition of claim 1.

16. The method of claim 15, wherein the cells are progenitor cells or stem cells.

17. The method of claim 16, wherein the stem cells are pluripotent stem cells, multipotent stem cells, somatic stem cells, mesenchymal stem cell, adipose-derived stem cell, endothelial stem cell, dental pulp stem cell, embryonic stem cells, bone marrow or hematopoietic stem cell, amniotic stem cells, lymphoid or myeloid stem cells.

18. A method of treating a wound or wound closure comprising applying a composition comprising a composition of claim 1 to the wound.

19. A wound dressing comprising a composition of claim 1.

20. The wound dressing of claim 19 selected from a bandage, gauze, cyanoacrylate glue, or suture.

21. The wound dressing of claim 19 further comprising an antibiotic.

* * * * *